(12) United States Patent
Lechmann et al.

(10) Patent No.: US 8,992,618 B2
(45) Date of Patent: Mar. 31, 2015

(54) INTERVERTEBRAL PROSTHESIS OR DISK PROSTHESIS

(75) Inventors: Beat Lechmann, Grenchen (CH); Robert Frigg, Bettlach (CH); Roger Buerki, Balsthal (CH)

(73) Assignee: DePuy Synthes Products, LLC, Raynham, MA (US)

( * ) Notice: Subject to any disclaimer, the term of this patent is extended or adjusted under 35 U.S.C. 154(b) by 2227 days.

(21) Appl. No.: 11/587,723

(22) PCT Filed: Apr. 26, 2004

(86) PCT No.: PCT/CH2004/000250
§ 371 (c)(1),
(2), (4) Date: Sep. 4, 2007

(87) PCT Pub. No.: WO2005/102226
PCT Pub. Date: Nov. 3, 2005

(65) Prior Publication Data
US 2008/0133015 A1  Jun. 5, 2008

(51) Int. Cl.
*A61F 2/44* (2006.01)
*A61F 2/30* (2006.01)
*A61F 2/46* (2006.01)

(52) U.S. Cl.
CPC ............. *A61F 2/447* (2013.01); *A61F 2/446* (2013.01); *A61F 2002/30777* (2013.01); *A61F 2002/30785* (2013.01); *A61F 2002/30789* (2013.01); *A61F 2002/30841* (2013.01); *A61F 2002/4475* (2013.01); *A61F 2002/448* (2013.01);

(Continued)

(58) Field of Classification Search
USPC ............... 623/17.11–17.16; 606/94
See application file for complete search history.

(56) References Cited

U.S. PATENT DOCUMENTS

| | | | |
|---|---|---|---|
| 4,338,925 A | 7/1982 | Miller | 606/94 |
| 4,405,249 A | 9/1983 | Scales | 606/93 |

(Continued)

FOREIGN PATENT DOCUMENTS

| | | |
|---|---|---|
| FR | 2 820 630 | 8/2002 |
| FR | 2836373 A1 * | 8/2003 |

(Continued)

OTHER PUBLICATIONS

U.S. Appl. No. 11/587,722—Non Final Office Action Dated Jun. 23, 2009.

(Continued)

*Primary Examiner* — Pedro Philogene
*Assistant Examiner* — Lynnsy Summitt
(74) *Attorney, Agent, or Firm* — Nutter McClennen & Fish LLP

(57) ABSTRACT

An intervertebral prosthesis or disk prosthesis comprising a front side, a rear side, an upper side which can be placed on the base plate of vertebral body, a lower side which can be placed on the base plate of a vertebral body, a right side, a left side, a cavity which can receive a fluid hydraulic osteocementum, an opening in the cavity and several outlets out from the cavity. The total of the transversal surfaces of the outlets SV on the front side, the total of the transversal surfaces of the outlets SH on the rear side, the total of the transversal surfaces of the outlets SR on the right side and the total of the transversal surfaces of the outlets on the left side satisfy the following conditions: SL>SR or SR>SL or SH>SV or SV>SH.

12 Claims, 7 Drawing Sheets

(52) U.S. Cl.
CPC .................... *A61F2002/4631* (2013.01); *A61F 2310/00353* (2013.01)
USPC .......................................... 623/17.16; 606/94

(56) References Cited

U.S. PATENT DOCUMENTS

| | | | | |
|---|---|---|---|---|
| 4,736,738 | A | 4/1988 | Lipovsek et al. | 606/88 |
| 5,214,987 | A | 6/1993 | Fenton | 81/460 |
| 5,571,189 | A | 11/1996 | Kuslich | 623/17.12 |
| 5,697,932 | A | 12/1997 | Smith et al. | 606/80 |
| 5,888,224 | A | 3/1999 | Beckers et al. | 623/17.16 |
| 6,039,761 | A * | 3/2000 | Li et al. | 623/17.16 |
| 6,048,343 | A | 4/2000 | Mathis et al. | 606/916 |
| 6,059,829 | A * | 5/2000 | Schlapfer et al. | 623/17.16 |
| 6,110,179 | A | 8/2000 | Flivik et al. | 606/99 |
| 6,123,705 | A * | 9/2000 | Michelson | 623/17.16 |
| 6,485,517 | B1 * | 11/2002 | Michelson | 623/17.11 |
| 6,645,213 | B2 | 11/2003 | Sand et al. | 606/92 |
| 6,676,664 | B1 | 1/2004 | Al-Assir | 606/94 |
| 6,726,722 | B2 * | 4/2004 | Walkenhorst et al. | 623/17.16 |
| 6,923,810 | B1 * | 8/2005 | Michelson | 606/247 |
| 7,156,877 | B2 | 1/2007 | Lotz et al. | 623/17.16 |
| 7,316,689 | B2 | 1/2008 | Lieberman | 606/93 |
| 7,361,193 | B2 * | 4/2008 | Frey et al. | 623/17.16 |
| 7,637,954 | B2 * | 12/2009 | Michelson | 623/17.11 |
| 7,655,027 | B2 | 2/2010 | Michelson | 606/279 |
| 2001/0005796 | A1 | 6/2001 | Zdeblick et al. | 623/17.11 |
| 2001/0032018 | A1 | 10/2001 | Castro et al. | 623/17.11 |
| 2002/0058947 | A1 | 5/2002 | Hochschuler et al. | 606/94 |
| 2002/0082700 | A1 * | 6/2002 | Bianchi et al. | 623/17.16 |
| 2002/0092871 | A1 | 7/2002 | Rickard et al. | 222/327 |
| 2002/0147497 | A1 | 10/2002 | Belef et al. | 623/17.12 |
| 2003/0036762 | A1 | 2/2003 | Kerr et al. | 606/93 |
| 2003/0100950 | A1 * | 5/2003 | Moret | 623/17.16 |
| 2004/0010260 | A1 | 1/2004 | Scribner et al. | 606/93 |
| 2004/0030389 | A1 | 2/2004 | Ferree | 623/17.15 |
| 2004/0186572 | A1 * | 9/2004 | Lange et al. | 623/17.11 |
| 2005/0038513 | A1 * | 2/2005 | Michelson | 623/17.11 |
| 2005/0070900 | A1 * | 3/2005 | Serhan et al. | 606/61 |
| 2005/0119747 | A1 * | 6/2005 | Fabris Monterumici et al. | 623/17.11 |
| 2005/0149192 | A1 * | 7/2005 | Zucherman et al. | 623/17.11 |
| 2005/0261781 | A1 * | 11/2005 | Sennett et al. | 623/23.54 |
| 2007/0161962 | A1 * | 7/2007 | Edie et al. | 604/257 |
| 2008/0071284 | A1 | 3/2008 | Lechmann et al. | 606/99 |

FOREIGN PATENT DOCUMENTS

| | | |
|---|---|---|
| WO | WO 97/23174 | 7/1997 |
| WO | WO 97/37619 | 10/1997 |
| WO | WO 01/56513 | 8/2001 |
| WO | WO 02/078514 | 10/2002 |

OTHER PUBLICATIONS

U.S. Appl. No. 11/587,722—Amendment in Response to Non Final Office Action.
U.S. Appl. No. 11/587,722—Final Office Action Dated Jan. 25, 2010.

* cited by examiner $$S_R = F_1 + F_2 + F_3$$

$$S_L = F_4 + F_5$$

INTERVERTEBRAL PROSTHESIS OR DISK PROSTHESIS

FIELD OF THE INVENTION

The invention relates to an intervertebral prosthesis or disk prosthesis that has a front side, a rear side, an upper side, a right side and a left side. The upper side may be suitable for resting against the baseplate of an intervertebral body and the lower side may be suitable for resting on the baseplate of an intervertebral body. The invention may also include a cavity suitable for accommodating a flowable hydraulic osteocementum. There may he an inlet opening into the cavity and several outlet openings emerging from the front side. The intervertebral or disk prosthesis is especially for arthrodesis surgery by means of dorsal access PLIF (posterior lumbar interbody fusion), TLIF (transforaminal lumbar interbody fusion), ELIF (extraforaminal lumbar interbody fusion), ALIF (anterior lumbar interbody fusion) and ACIF (anterior cervical interbody fusion). The objective of this surgical technique is the treatment of a degenerated or otherwise diseased intervertebral disk. The surgeon looks for access to the intervertebral disk through a centrally placed skin incision. Subsequently, he exposes the rear region of the movement segments, especially the laminae and the pedicle entry points. By means of a partial resection of the facettal and laminar components, the surgeon aims past the nerve roots and the medullary space in the direction of the discased intervertebral disk.

BACKGROUND OF THE INVENTION

For this surgical technique, only a limited amount of autologous spongiosa is available for filling the cavities of cage-like intervertebral or disk prosthesis and the spaces between individual implants and their surroundings. In the long term, the arthrodesis takes place not with the implant but between the bone and the bone replacement material. The individual implants therefore function only as place holders or spacers.

The intervertebral spaces, supplied with the known intervertebral implants, therefore frequently do not attain complete arthrodesis, that is, they end in a pseudoarthrosis. The situation is much the same also with cage-like intervertebral implants for the cervical spine, as well as for those, which were inserted through ventral entrances. Such intervertebral spaces are not stable mechanically, as would have been expected from a stiffening. The consequences then may be recurring pain with subsequent revision surgery.

For the implants and surgical techniques described above, the surgeon uses autologous bone material, which he obtains from the resected parts of the vertebral body or by means of an additional intervention in the crest of the ilium. Since dorsal accesses to the intervertebral disk space are very narrow, the applying of bone material is made difficult. The surgeon is unable to ensure that the whole of the intervertebral space is filled with autologous bone material. There is therefore the danger that empty spaces will result which, on the one hand, permits migration of the implant. On the other hand, the spaces, not filled with autologous bone material, are filled by a soft, fibrous tissue.

SUMMARY OF THE INVENTION

It is an object of the invention to provide an intervertebral prosthesis or a disk prosthesis, which makes an asymmetric emergence of the osteocementum possible, so that individual regions between the vertebral bodies (for example the central and posteriors zones) are automatically supplied with more osteocementum than other regions.

This objective is accomplished by an intervertebral prosthesis or disc prosthesis, for which the outlet openings are dimensioned differently in size. The amount of osteocementum $K_L$, emerging through $S_L$ is either larger or smaller than the amount of osteocementum $K_R$ emerging through $S_R$; or the amount of osteocementum $K_H$, emerging through $S_H$, is larger or smaller than the amount of osteocementum $K_V$ emerging through $S_V$.

In other words, the outlet openings are dimensioned so that, when flowable osteocementum is supplied through the inlet opening into the cavity, the amount of osteocementum $K_L$ emerging through $S_L$ is either larger or smaller than the amount of osteocementum $K_R$ emerging through $S_R$ or the amount of osteocementum $K_H$, emerging through $S_H$, is larger or smaller than the amount of osteocementum $K_V$, emerging through $S_V$.

The invention permits the intervertebral space to be filled with synthetic bone material (osteocementum) after the cage-like intervertebral prosthesis or disk prosthesis has been placed. The implant is secured by the emergence and subsequent curing of the flowable, hydraulic osteocementum. Due to the asymmetric arrangement of the outlet openings in the implant, the osteocementum can be spread selectively. The inventive prosthesis furthermore has the advantage that it makes superfluous the additional removal of bone at the crest of the iliac, which can cause long enduring pain.

In a special embodiment, the inlet opening is provided in the front side of the prosthesis and the cavity extends from the inlet opening in the direction of the rear side.

In the case of a further embodiment, the inlet opening is disposed in the left all right side of the prosthesis and the cavity extends from the inlet opening in the direction of the opposite right or left side.

In the case of a further embodiment, the cross section of the cavity decreases at least on a partial section as the distance from the inlet opening increases. Due to the tapering of the cavity, the liquid cement mixture flows more easily through the side openings of the implant. The wall of the implant in the opening opposite the injection point has a shearing-off edge, so that the liquid cement mixture is diverted.

In the case of a further embodiment, the cavity tapers, at least on a partial section, either in wedge-shaped or conical fashion. In the case of a further embodiment, the upper and lower sides converge in the direction of the front side at least on a partial section. In yet another embodiment, the prosthesis is filled at least partially with a cured hydraulic osteocementum, which extends at least partially beyond the outlet opening.

In the case of a further embodiment, the implant may consist of two intervertebral prostheses, which are disposed next to one another, the right side of the intervertebral prosthesis disposed on the left being oriented in the direction of the left side of the intervertebral prosthesis disposed on the right. For the intervertebral prosthesis disposed on the left, the condition $S_L > S_R$ applies and for the intervertebral prosthesis on the right, the condition $S_R > S_L$.

Moreover, the intervertebral prosthesis may be varied in many ways, for example, by using flat, concave, convex or also spherical side walls.

Calcium phosphate cements, which, after the two components are mixed, may be injected in liquid form into the implant and are subsequently cured hydraulically, are suitable as flowable hydraulic osteocementum.

BRIEF DESCRIPTION OF THE DRAWINGS

The invention and further development of the invention are described in even greater detail by means of several examples and partially diagrammatic drawings, in which.

DETAILED DESCRIPTION OF THE PREFERRED EMBODIMENTS

Figure 1:
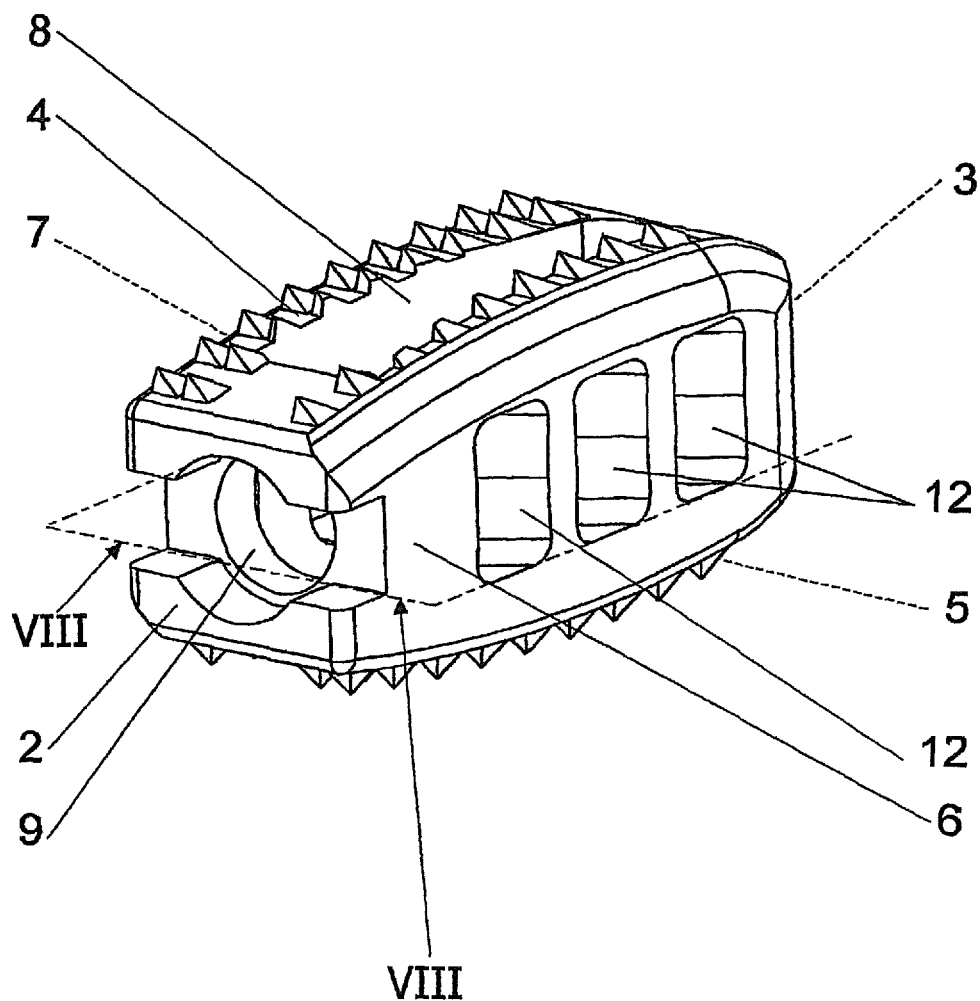
FIG. 1 shows a perspective view of an inventive, lens-shaped intervertebral implant.
Figure 2:
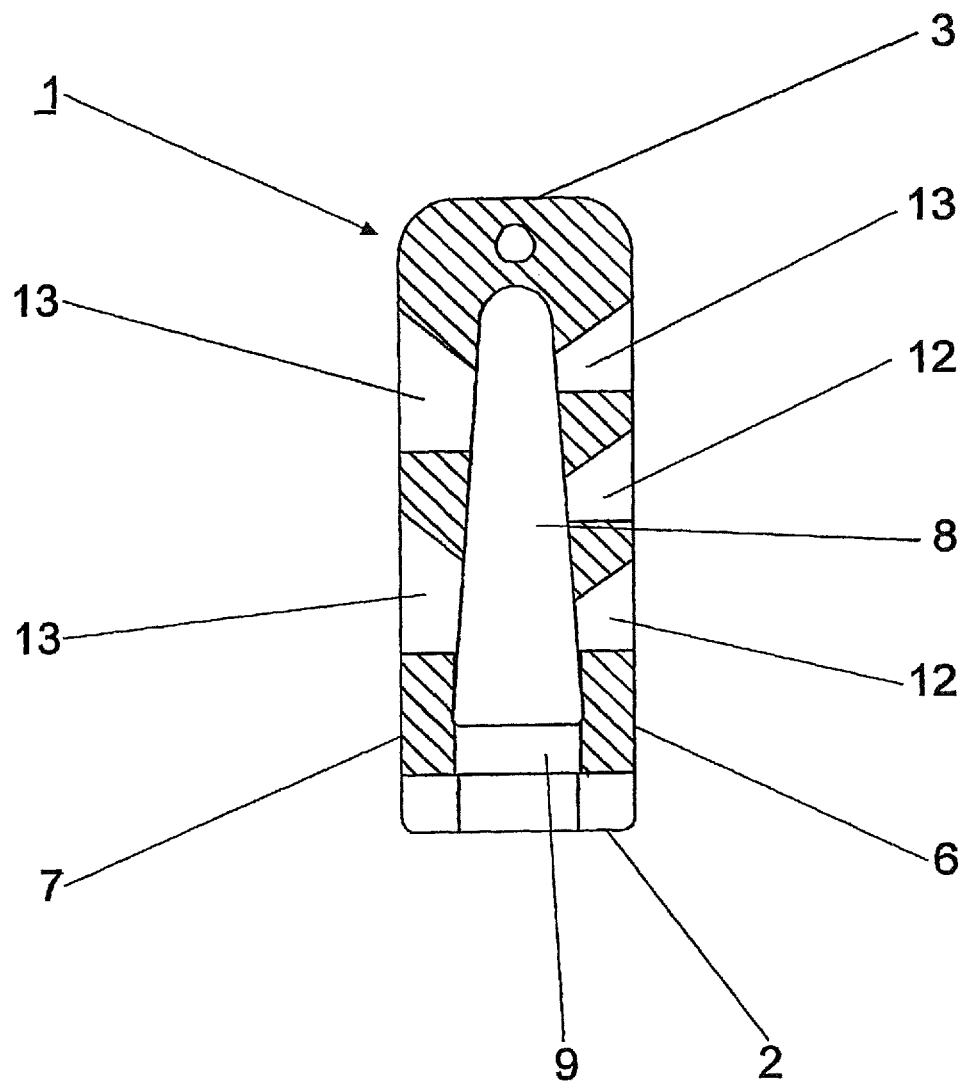
FIG. 2 shows a longitudinal section through the intervertebral implant of FIG. 1 along the central plane VIII-VIII.

The intervertebral prosthesis 1, shown in FIGS. 1 and 2, consists of a rectangular hollow body and has a front side 2, a rear side 3, an upper side 4 suitable for positioning against the baseplate of a vertebral body, a lower side 5 suitable for positioning against the baseplate of a vertebral body, a right side 6, a left side 7, a cavity 8 suitable for accommodating a flowable, hydraulic osteocementum, an inlet opening 9 into the cavity 8 and several outlet openings 10; 11; 12; 13 from the cavity 8. The upper side 4 and the lower side 5 converge toward the front side 2 as well as toward the rear side 3, so that a lens-like configuration of the intervertebral prosthesis results.

As can be seen from FIG. 2, the cross section of the cavity 8 decreases in the shape of a cone as the distance from the inlet opening 9 increases.

Figure 3:
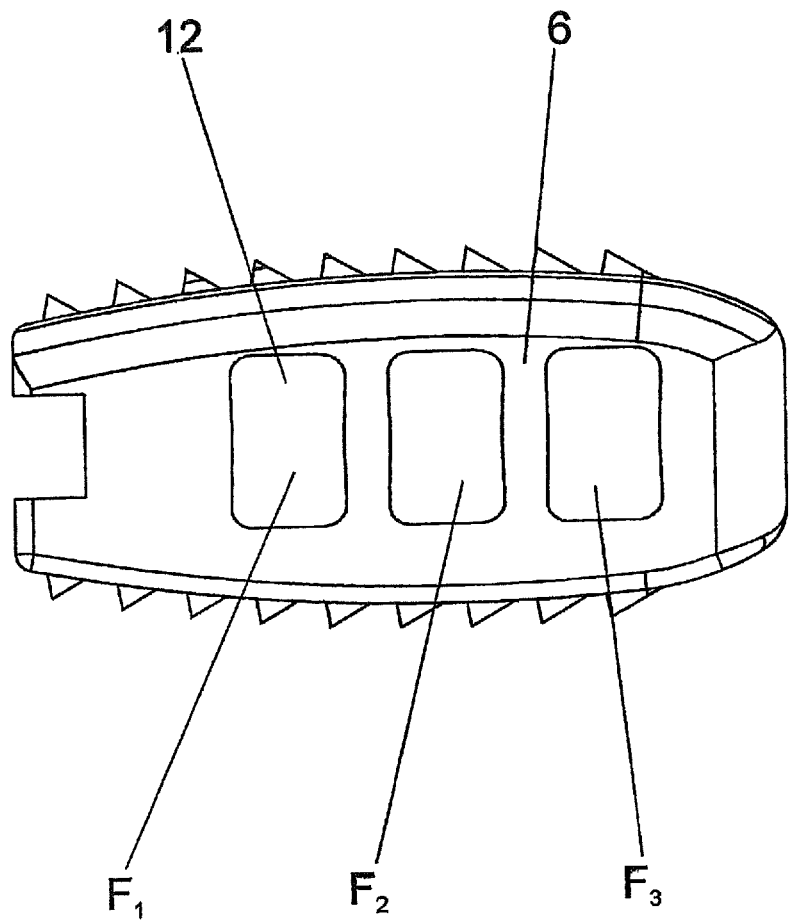
FIG. 3 shows a side view from the right of the intervertebral implant of FIG. 1.

As shown in FIG. 3, there are three outlet openings 12 with areas $F_1$, $F_2$ and $F_3$ in the right side 6 of the intervertebral prosthesis 1, so that the sum $S_R$ of the cross sectional surfaces of the outlet openings emerging the right side 6 is $S_R=F_1+F_2+F_3$.

Figure 4:
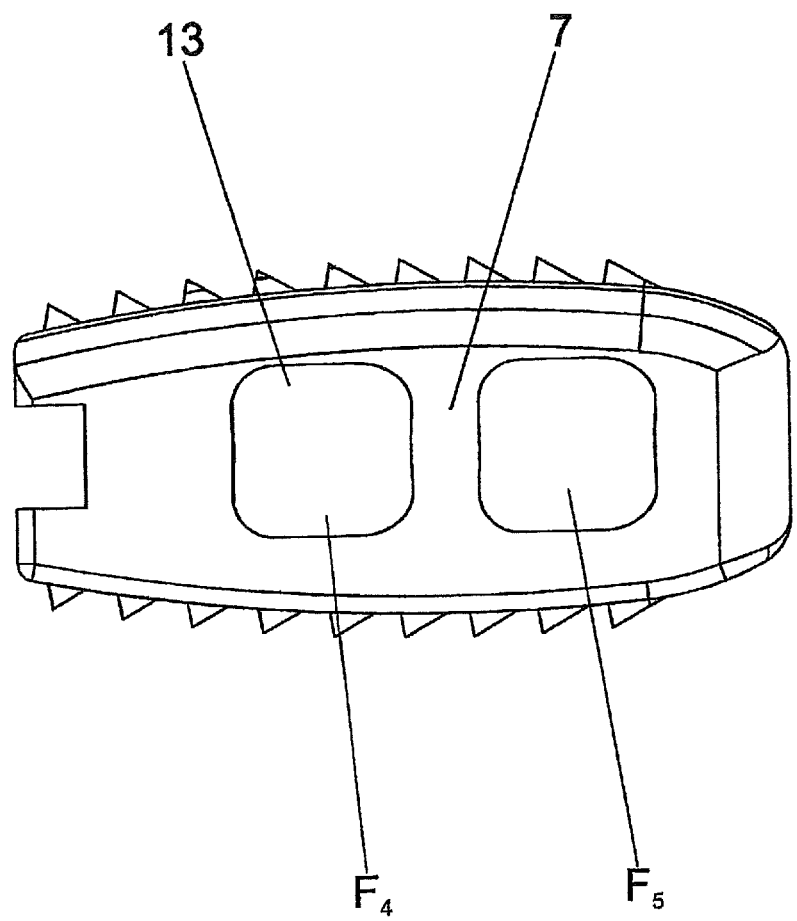
FIG. 4 shows a side view from the left of the intervertebral implant of FIG. 1.

As shown in FIG. 4, there are two outlet openings 13 with the areas $F_4$ and $F_5$ in the left side 7 of the intervertebral prosthesis 1, so that the sum $S_L$ of the cross-sectional surfaces of the outlet openings emerging for the left side 7 is $S_L=F_4+F_5$.

It is important that the sum $S_L>S_R$, so that more osteocementum can emerge on the left side 7 of the intervertebral prosthesis 1 from the cavity 8 through the outlet opening 13 into the intervertebral space than from the right side 6.

Figure 5:
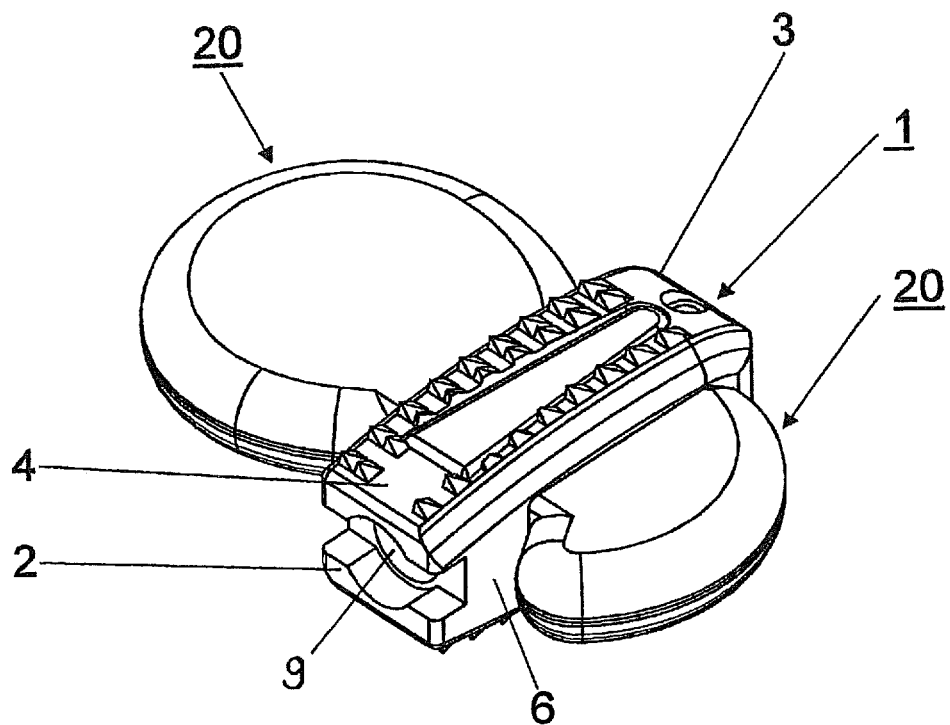
FIG. 5 shows a perspective view of an inventive intervertebral prosthesis, which is secured by means of cured osteocementum.
Figure 6:
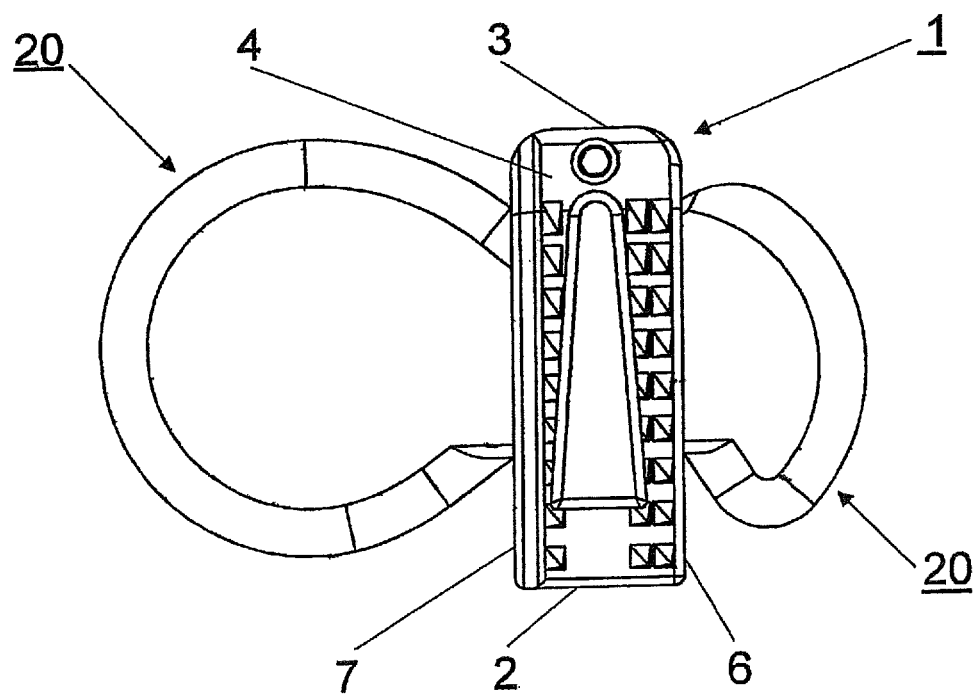
FIG. 6 shows a plan view of the intervertebral prosthesis of FIG. 5.

FIGS. 5 and 6 show how the osteocementum 20, emerging from the right side 6 and the left side 7 of the intervertebral prosthesis 1, is distributed. Because the sum $S_L$ of the cross sectional areas of the outlet openings 13 emerging on the left side 7 is larger, the amount of osteocementum 20, emerging on the left side 7 and curing, is also larger than that emerging on the right side 6 and curing.

Figure 7:
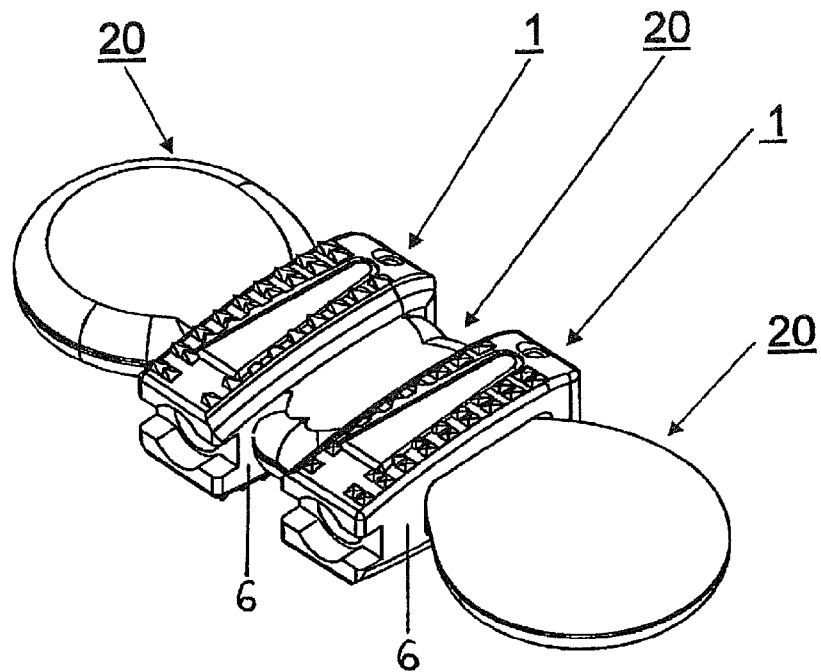
FIG. 7 shows a perspective view of a variation of the embodiment, using two intervertebral implants, the osteocementum securing the implant in their position relative to one another as well as to prevent migrating apart.
Figure 8:
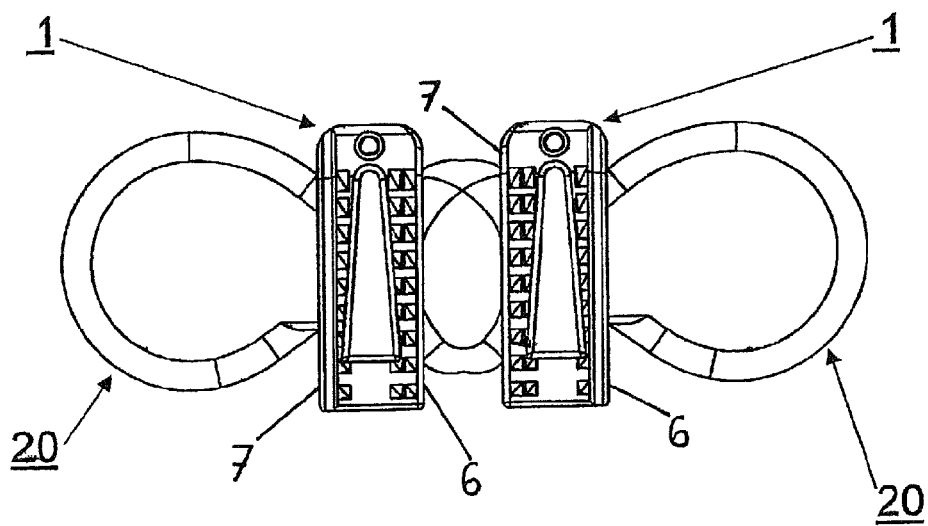
FIG. 8 shows a plan view of the two intervertebral implants of FIG. 7.

FIGS. 7 and 8 show a further embodiment, which consists of two inventive intervertebral prosthesis 1, which are disposed next to one another. The two intervertebral prostheses are positioned in such a manner, that the right side 6 of the intervertebral prosthesis 1, which is disposed on the left, is oriented in the direction of the left side 7 of the intervertebral prosthesis 1, which is disposed on the right. For the intervertebral prosthesis 1, disposed on the left, the condition $S_L>S_R$ applies, whereas, for the intervertebral prosthesis 1, which is disposed on the right, the reverse applies, namely $S_R>S_L$. Due to this measure, less osteocementum 20 emerges in the space between the two intervertebral prostheses 1 than emerges to the right side of the intervertebral prosthesis 1 disposed on the right and to the left side 7 of the intervertebral prosthesis 1 disposed on the left.

Figure 9:
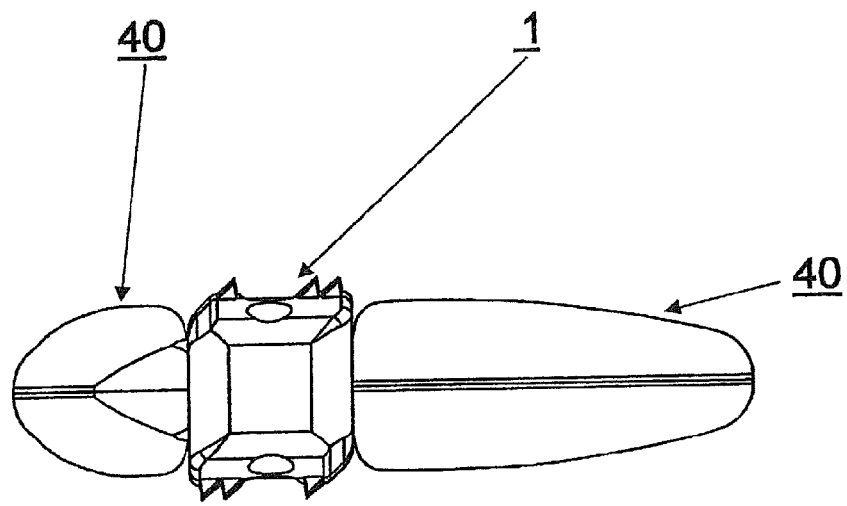
FIG. 9 shows a front view of a variation of the embodiments, in which the perforated intervertebral implant has a rectangular cross section

FIG. 9 shows a variation of the embodiment of an inventive intervertebral implant 1, which has a rectangular cross section and from which a larger amount of osteocementum 40 has emerged on the right side than on the left side.

Figure 10:
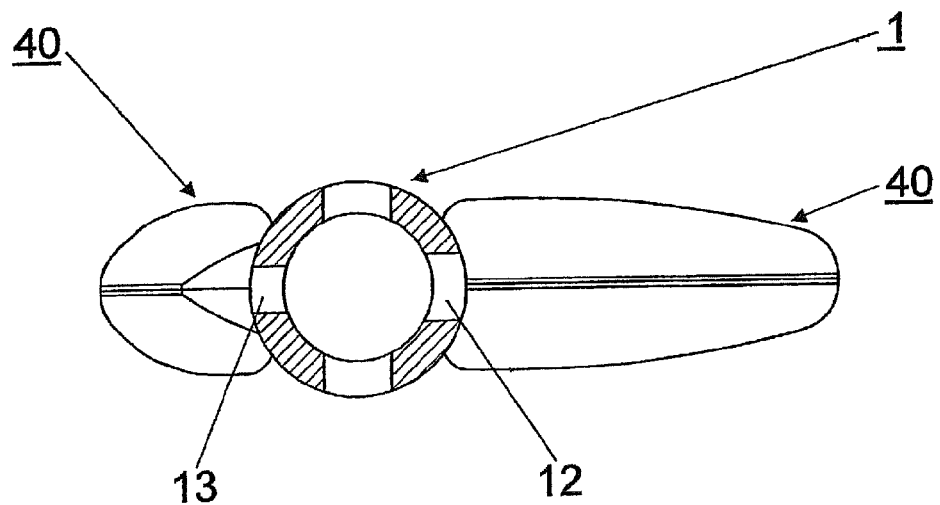
FIG. 10 shows a front view of a variation of the embodiment, in which the perforated intervertebral implant has a circular ring-shaped cross section.

FIG. 10 shows a further variation of an embodiment of an intervertebral prosthesis 1, which has a circular cross section and for which the amount of osteocementum 40 emerging on the right side through the outlet openings 12 is larger than that emerging on the left side through outlet openings 13.

The invention claimed is:

1. An intervertebral implant system comprising:
    an intervertebral implant for implantation between an upper vertebra and a lower vertebra;
    a volume of flowable osteocementum; and
    an insertion tool for conveying the flowable osteocementum to the intervertebral implant;
    wherein the implant includes: a cavity defined by a body having a first end for engaging the insertion tool, the first end having an inlet opening for receiving the flowable osteocementum; a top surface for contacting at least a portion of the upper vertebra; a bottom surface for contacting at least a portion of the lower vertebra; a second end opposite the first end; a first lateral side being substantially straight and having a first length and at least one outlet, the at least one outlet having a combined cross-sectional area A1; a second lateral side being substantially straight and having a second length and at least one outlet, the at least one outlet of the second side having a combined cross-sectional area A2; wherein the first length is substantially the same as the second length and A1 is not equal to A2 thereby providing that the flowable osteocementum emerges asymmetrically, and wherein the second end is dosed so that the flowable osteocementum cannot emerge therefrom.

2. The implant of claim 1, wherein A1 is greater than A2 so that the volume of osteocementum flowing through the first side is greater than the volume of osteocementum flowing through the second side.

3. The implant of claim 2, further comprising a second intervertebral implant including
    a cavity defined by a body having a first end for engaging an insertion tool, the first end having an inlet opening for receiving the flowable osteocementum; a top surface for contacting at least a portion of the upper vertebra; a bottom surface for contacting at least a portion of the lower vertebra; a second end opposite the first end; a first side having at least one outlet, the at least one outlet having a combined cross-sectional area A1; a second side having at least one outlet, the at least one outlet having a combined cross-sectional area A2; wherein A1 is greater than A2 thereby providing that the flowable osteocementum emerges asymmetrically and the second intervertebral implant is configured to be implanted adjacent to the first intervertebral implant such that the second side of the first intervertebral implant is facing the second side of the second intervertebral implant, and wherein the second end is closed so that the flowable osteocementum cannot emerge therefrom.

4. The implant of claim 1, wherein the cavity comprises a cross-sectional area.

5. The implant of claim 4, wherein the cavity extends from the inlet opening towards the second end.

6. The implant of claim 5, wherein the cross-sectional area of the cavity decreases as the distance from the inlet opening increases.

7. The implant of claim 6, wherein the cross-sectional area of the cavity decreases in one of a wedge-shaped or a conical shape.

8. The implant of claim 1, wherein the top surface and the bottom surface converge towards the second end at least on a partial section.

9. An intervertebral implant system comprising:
an intervertebral implant for implantation between an upper vertebra and a lower vertebra;
a volume of flowable osteocementum; and
an insertion tool for conveying the flowable osteocementum to the intervertebral implant;
wherein the implant includes a body having a top surface for contacting at least a portion of the upper vertebra; a bottom surface for contacting at least a portion of the lower vertebra; a first end for engaging the insertion tool, the first end having an inlet opening for receiving the flowable osteocementum; a second end opposite the first end; an internal cavity with a cross-sectional area, the internal cavity extending from the inlet opening in the direction of the second end; a first lateral side being substantially straight and having a first length and at least one outlet, the outlets having a combined cross-sectional area A1; a second lateral side being substantially straight and having a second length and at least one outlet, the outlets of the second side having a combined cross-sectional area A2; wherein the first length is substantially the same as the second length and A1 is greater than A2 thereby providing that the flowable osteocementum emerges asymmetrically and such that when osteocementum flows through the implant, the volume of osteocementum that flows through the first side is greater than the volume of osteocementum that flows through the second side, and wherein the second end is closed so that the flowable osteocementum cannot emerge therefrom.

10. The implant of claim 9, wherein the cross-sectional area of the cavity decreases as the distance from the inlet opening increases.

11. The implant of claim 9, wherein the cross-sectional area of the cavity decreases in one of a wedge-shape or a conical shape.

12. The implant of claim 9, wherein the top surface and the bottom surface converge towards the second end at least on a partial section.

* * * * *